United States Patent
Armini

(10) Patent No.: US 6,183,409 B1
(45) Date of Patent: Feb. 6, 2001

(54) SOFT X-RAY EMITTING RADIOACTIVE STENT

(75) Inventor: Anthony J. Armini, Manchester-by-the Sea, MA (US)

(73) Assignee: Implant Sciences Corporation, Wakefield, MA (US)

( * ) Notice: Under 35 U.S.C. 154(b), the term of this patent shall be extended for 0 days.

(21) Appl. No.: 09/247,198

(22) Filed: Feb. 9, 1999

Related U.S. Application Data

(60) Provisional application No. 60/074,181, filed on Feb. 10, 1998.

(51) Int. Cl.⁷ .................................................... A61N 5/00
(52) U.S. Cl. ............................................................ 600/3
(58) Field of Search ..................... 600/3, 1–8; 606/130; 424/1.29

(56) References Cited

U.S. PATENT DOCUMENTS

| | | |
|---|---|---|
| 3,351,049 | 11/1967 | Lawrence . |
| 4,323,055 | 4/1982 | Kubiatowicz . |
| 4,733,665 | 3/1988 | Palmaz . |
| 4,739,762 | 4/1988 | Palmaz . |
| 4,776,337 | 10/1988 | Palmaz . |
| 4,881,938 | 11/1989 | van't Hooft . |
| 4,946,435 | 8/1990 | Suthanthiran et al. . |
| 5,030,194 | 7/1991 | Van't Hooft . |
| 5,059,166 | 10/1991 | Fischell et al. . |
| 5,176,617 | 1/1993 | Fischell et al. . |

(List continued on next page.)

FOREIGN PATENT DOCUMENTS 0 593 136 A1   12/1990   (EP) .

OTHER PUBLICATIONS

Mumper et al., "Neutron–Activated Holmium–166–Poly (L–Lactic Acid) Microspheres: A Potential Agent for the Internal Radiation Therapy of Hepatic Tumors," *The Journal of Nuclear Medicine*, No. 11 Nov. (1991), pp. 2139–2143.

Cheng et al., "Neutron–Activatable Glass Seeds for Brachytherapy," Department of Nuclear Engineering and Research Reactor, University of MO–Columbia, Columbia, MO and Department of Ceramic Engineering, University of MO–Rolla, Rolla, MO (Abstract No. 994).

Kagehira et al., "Dose Evaluation in Gadolinium Neutron Capture Therapy," Kyoto Daigaku Genshiro Jikkensho Gakujutsu Koenkai Hobunshu (1994), 28, pp. 187–96, Japan (Abstract only).

(List continued on next page.)

*Primary Examiner*—Max Hindenburg
*Assistant Examiner*—Brian Szmal
(74) *Attorney, Agent, or Firm*—Foley, Hoag&Eliot, LLP; David P. Halstead

(57) ABSTRACT

An implantable medical device according to the present invention comprises a body, such as a stent or a wire, and an isotope having a high neutron activation cross-section, such as $^{168}$Yb or $^{124}$Xe, ion-implanted onto the surface of the body. The use of isotopes having high neutron activation cross-sections allows a wider choice of substrates to be employed, including stainless steel, nickel, titanium, and alloys including these metals, because the time required for neutron activation of the device is reduced. A coating of high-density material may be incorporated to serve several useful purposes, including containment of undesirable beta particles from long-lived radioactive species, creation of a biologically inert surface, and enhancement of x-ray radiopacity to improve the visibility of an implanted medical device. The implantable medical devices of the present invention also comprise radioactive medical devices which include radioisotopes such as $^{169}$Yb and $^{125}$I.

13 Claims, 2 Drawing Sheets

U.S. PATENT DOCUMENTS

| | | | |
|---|---|---|---|
| 5,302,369 | * | 4/1994 | Day et al. .............................. 424/1.29 |
| 5,342,283 | | 8/1994 | Good . |
| 5,364,336 | * | 11/1994 | Carr ........................................ 600/2 |
| 5,382,261 | | 1/1995 | Palmaz . |
| 5,607,442 | | 3/1997 | Fischell et al. . |
| 5,632,771 | | 5/1997 | Boatman et al. . |
| 5,656,036 | | 8/1997 | Palmaz . |
| 5,674,177 | | 10/1997 | Hehrlein et al. . |
| 5,868,757 | * | 2/1999 | Koutrouvelis ......................... 606/130 |
| 5,919,126 | * | 7/1999 | Armini ..................................... 600/3 |

OTHER PUBLICATIONS

Nath et al., "Dosimetric Characteristics of a Double Wall Iodine–125 Source for Interstitial Brachytherapy," Med. Phys. (1993), 20(5), pp. 1475–83 (Abstract only).

MacPherson et al., "Dose Distributions and Dose Rate Constants for New Yterbium–169 Brachytherapy Seeds," Medical Physics (New York) (1995) vol. 22, No. 1, pp., 89–96 (Abstract only).

* cited by examiner

SOFT X-RAY EMITTING RADIOACTIVE STENT

RELATED APPLICATIONS

This application is based on and claims priority to provisional application Ser. No. 60/074,181 filed Feb. 10, 1998, the entire disclosure of which is hereby incorporated herein by reference.

BACKGROUND

After balloon angioplasty, a metal tubular scaffold structure called a stent may be permanently implanted to physically hold open the repaired coronary artery. Unfortunately, up to 30% of such procedures result in narrowing or reclosure (restenosis) of the artery within six months to one year. One solution to the problem is to provide acute local, postoperative radiation treatment of the site using a catheter tipped with iridium-192 radioisotope. In this method, called intra-vascular brachytherapy, the iridium-192-tipped catheter is placed at the arterial site for thirty to forty minutes after stent deployment and then retracted. This type of acute high dose treatment using gamma radiation has been found to substantially reduce the rate of subsequent restenosis, as noted in Wiedermann, J. G. et al., "Intracoronary Irradiation Markedly Reduces Restenosis After Balloon Angioplasty in a Porcine Model," 23 J. Am. Coll. Cardiol., 1491–1498 (May 1994) and Teirstein, P. S. et al., "Catheter-Based Radiotherapy to Inhibit Restenosis After Coronary Stenting," 336 New England Journal of Medicine, 1697–1703 (Jun. 12, 1997).

This method of irradiating the patient suffers from the hazards associated with the required high radiation intensity. In addition to the surgeon, an oncologist and a radiation physicist are typically required for the procedure. A heavily shielded lead vault is needed to separate the patient from the operating room personnel, and the task of safely inserting the catheter containing the intense source, which is on the order of about 0.2 Curies, is particularly difficult. If irregularities occur in the procedure, the surgeon has relatively little time to respond, and therefore emergency procedures must be well-rehearsed. It is felt that this method, while possible in a research environment, may not be practical for normal usage.

An alternate method of addressing the restenosis problem is to use a permanently implanted radioactive stent, the method preferred by most physicians for its greater safety. Sources of radiation which are either pure beta particle or x-ray emitters are preferred because of the short range of the radiation, thus automatically protecting both the patient and the operating room personnel, particularly after the arterial insertion of the stent on the catheter.

As a result of studies in rabbits and swine, it is believed that a total dose of between 15 and 25 Grays is required to successfully inhibit restenosis in coronary arteries. Existing radioactive stent designs utilizing ion implantation of radioisotopes such as $^{32}$P, $^{186}$Re, $^{90}$Y or $^{103}$Pd require a highly specialized facility to perform the activations at considerable cost. U.S. Pat. Nos. 5,050,166 and 5,376,617 to Fischell et al. describe radioactive stents wherein radioactive material is either placed within the stent body or is electroplated onto the surface. Other methods involving cyclotron irradiation or coatings with radioactive liquids have contamination and safety problems respectively. Handling radioactive materials in these methods is difficult, expensive, and risky.

To avoid such difficult procedures, it is possible to ion-implant or coat a stent with a stable isotope, such as $^{31}$P, $^{185}$Re, $^{89}$Y, or $^{102}$Pd, which can be activated by neutron bombardment in order to generate a radioisotope, such as $^{32}$P, $^{186}$Re, $^{90}$Y, or $^{103}$Pd, respectively. In this manner, the stent would be fabricated in the absence of any radioactive species and then activated prior to implantation into the patient. The material used for the body of the stent to be activated must be carefully selected not to include elements that are easily activated by neutron bombardment to produce isotopes that give off undesirable radiation. For example, stainless steel, an otherwise ideal material, cannot be used in the above method because the neutron bombardment will activate the stent body to produce long-lived, high-energy gamma ray-emitting isotopes such as $^{51}$Cr and $^{59}$Fe, which are unacceptable in a permanently implanted stent.

Even small impurities in otherwise acceptable metals may give rise to harmful radiation. For example, Laird ("Inhibition of Neointinol Proliferation with Low-Dose Irradiation from a β-Particle-Emitting Stent", Laird J. R. et al., Circulation, 93, No. 3, February 1996) ion-implanted a titanium stent with stable $^{31}$P and generated the radioisotope $^{32}$P by inserting the ion-implanted stent in a nuclear reactor. This technique produced only a very small amount of $^{32}$P, and the trace impurities in the titanium body produced high energy gamma rays which were comparable in strength to the desired $^{32}$P radiation. This technique suffered from the fact that $^{31}$P has a very small neutron activation cross-section (0.18 barns), and thereby requires a long activation time. Even though titanium itself does not activate with thermal neutrons to form long-lived radioisotopes, titanium does activate with fast neutrons to $^{46}$Ti, having a long half-life of 83 days, and the high cross-section impurities in the titanium body produced too much harmful contaminating gamma radiation. These experiments on titanium stents suggest that ion implantation of stable isotopes into stainless steel stents would present even greater obstacles.

SUMMARY OF THE INVENTION

The present invention comprises radioactive, x-ray-emitting medical devices for temporary or permanent implantation and methods of preparing such devices. The methods of the present invention reduce the generation of undesirable radioisotopes by ion implanting a stable isotope having a very high neutron activation cross-section, e.g., at least about 180 barns, or at least about 3000 barns, and then activating the stable isotope by thermal neutron activation to form a radioactive isotope. In a currently preferred embodiment, an implantable therapeutic medical device is prepared by ion-implanting the stable isotope $^{168}$Yb, which has a thermal neutron cross-section of 3470 barns, into the body of the device and activating the $^{168}$Yb atoms in a nuclear reactor for a time sufficient to produce $^{169}$Yb, a soft x-ray emitter with a half-life of approximately 32 days. In an alternate embodiment, a temporarily implanted device is prepared by ion-implanting $^{124}$Xe, which has a thermal neutron activation cross-section of 193 barns, into the outside surface of a wire. Thermal neutron activation of $^{124}$Xe generates $^{125}$I, a soft X-ray emitter with a half-life of 60 days.

A medical device according to a preferred embodiment of the invention comprises a substrate or body comprising $^{168}$Yb, $^{169}$Yb, $^{124}$Xe, or $^{125}$I associated with the body, such as disposed on, incorporated within, or carried with the body. Preferably, the device comprises between about $1 \times 10^{15}$ and about $5 \times 10^{17}$ $^{168}$Yb atoms. In certain embodiments, the device comprises a concentration of $^{168}$Yb at least about $1 \times 10^{16}$ atoms/cm$^2$. In a currently preferred embodiment, the medical device comprises a stent.

In an alternate embodiment, wherein the body comprises a source wire, between about $1\times10^{17}$ and about $5\times10^{18}$ atoms of $^{124}$Xe per centimeter of length are associated with the wire.

The stable isotope can be any isotope having a sufficiently large neutron activation cross-section so that upon thermal neutron activation, it forms a radioactive isotope having a desirable emission profile in a sufficiently short time that concurrent activation of undesirable isotopes from metals in the body is minimized or avoided. Exemplary isotopes having this property are $^{124}$Xe and $^{168}$Yb, which are currently preferred.

The body refers to that portion of the device which comprises the underlying structure of said device. The body may be formed from any material suitable for use in medical devices, particularly in implantable medical devices. In a preferred embodiment, the body is formed from one or more materials selected from the group consisting of metals and metal alloys, organic polymers, and ceramic oxides. Suitable metals and metal alloys comprise, for example, stainless steel, rhodium titanium, chromium, nickel, nitinol, rhenium, and rhenium alloys. Preferred materials comprise stainless steel, rhodium, nitinol, titanium, palladium, and alloys thereof.

The devices of the present invention may further comprise a high-density coating. In a preferred embodiment, the high-density coating comprises at least one material selected from the group consisting of titanium, palladium, ytterbium, vanadium, manganese, copper, praseodymium, and rhodium. Preferred materials include titanium, rhodium, and palladium. The high-density coating preferably has a thickness greater than the range of 70 keV beta particles. The high-density coating is preferably between approximately 0.01 micrometers thick and approximately 10 micrometers thick.

In another embodiment of the invention, an adhesion coating may be disposed between the body and the high density coating. Said adhesion coating is useful for improving the adhesion of the high-density coating to the body. The adhesion coating preferably comprises at least one material selected from the group consisting of aluminum, silicon, titanium, vanadium, palladium, ytterbium, manganese, copper, nickel and rhodium.

The invention also comprises methods for making medical devices. In one aspect, the method comprises contacting the body with a stable (i.e., non-radioactive) isotope having a high neutron-activation cross-section such as $^{168}$Yb or $^{124}$Xe under conditions sufficient to cause the element to become disposed on, associated with, or carried with the body. The body and the isotope are then exposed to a source of thermal neutrons under conditions sufficient to induce activation of the stable isotope, thereby forming a radioactive isotope having a desirable emission profile. In a currently preferred embodiment, wherein $^{168}$Yb is used as the stable isotope, thermal neutron activation induces formation of $^{169}$Yb, a radioactive isotope having a half-life of about 32 days. In an alternate embodiment, wherein $^{124}$Xe is used as the stable isotope, thermal neutron activation induces formation of $^{125}$I, radioisotope having a half-life of about 60 days. The first step of the method may be performed by any suitable method for applying elements to a body or substrate, including, for example, ion-implanting the elements into the body, coating the elements onto the surface of the body, sputtering the elements onto the surface of the body, applying the elements to the body by physical vapor deposition, electroplating the elements onto the surface of the body, or some combination thereof. In a preferred embodiment, the isotope is applied using ion implantation, more preferably during application of a coating of a second metal for increased convenience and reproducibility. The second metal may be any metal suitable for a high-density coating, preferably titanium, palladium, or rhodium.

The second step, wherein the implanted isotopes are activated, preferably is carried out under conditions which induce activation of $^{168}$Yb to form $^{169}$Yb or which induce activation of $^{124}$Xe to form $^{125}$I, while minimizing generation of undesirable radioisotopes by activation of metals within the body. In a currently preferred embodiment, a device ion-implanted with $^{168}$Yb is exposed to a source of thermal neutrons for about two hours or less, thereby producing a sufficient therapeutic amount of $^{169}$Yb while substantially avoiding formation of undesirable radioisotopes from the elements in the body. In another currently preferred embodiment, a device ion-implanted with $^{124}$Xe is exposed to a source of thermal neutrons, thereby producing a sufficient therapeutic amount of $^{125}$I while substantially avoiding formation of undesirable radioisotopes from the elements in the body.

A second aspect of the present method further comprises contacting the body with a radioactive isotope, thereby avoiding the thermal neutron activation step. In a preferred embodiment, the body is contacted with $^{169}$Yb or $^{125}$I under conditions sufficient to cause the $^{169}$Yb or $^{125}$I to become disposed on, associated with, or carried with the body.

The foregoing methods of the present invention may further comprise the step of applying a high-density coating. The high-density coating may be applied to at least a portion of the body by any coating method, for example by sputtering, physical vapor deposition, electroplating, or some combination thereof. The high-density coating may be applied at any point in the process after the first step. In a preferred embodiment, an adhesion coating is applied prior to applying the high-density coating.

Figure 1A:
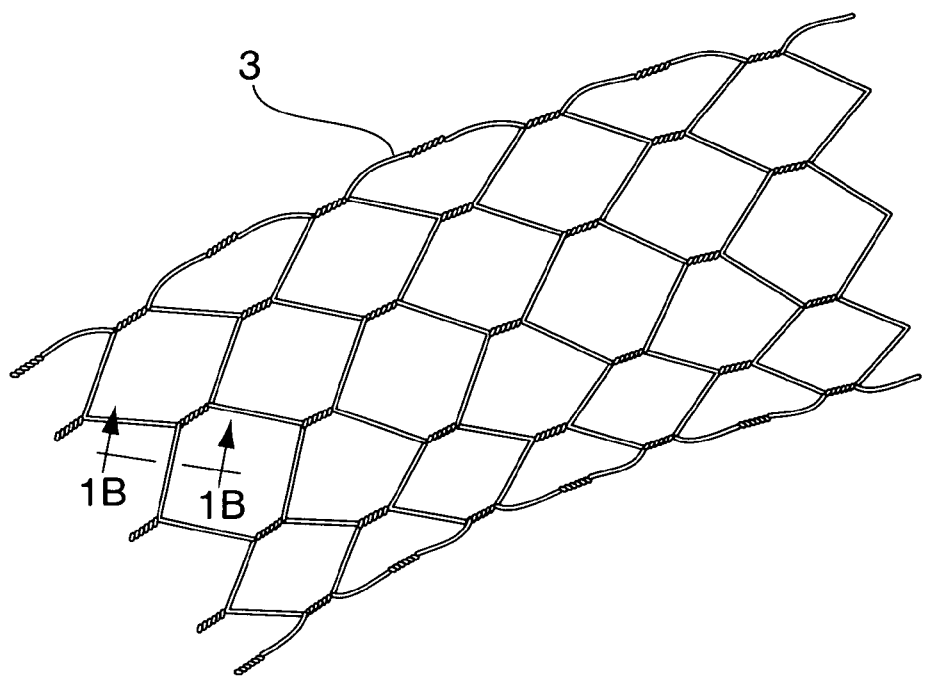
FIG. 1 illustrates a side-view and a cross-section of a single wire of a tubular mesh stent, an embodiment of the present invention.

DETAILED DESCRIPTION OF THE
PREFERRED EMBODIMENTS

The present invention overcomes the problems associated with neutron activation of non-radioactive precursor elements disposed on substrates which themselves are susceptible to neutron activation by employing a stable isotope having a large neutron activation cross-section, e.g., greater than about 180 barns, or greater than about 3000 barns, as the non-radioactive precursor. Currently preferred isotopes are $^{124}$Xe and $^{168}$Yb, although other isotopes having similar properties can be used. For example, activating $^{168}$Yb atoms, which have a neutron activation cross-section of 3470 barns, in a nuclear reactor produces $^{169}$Yb, a soft x-ray emitter with a half-life of 32 days. The $^{168}$Yb or $^{124}$Xe preferably is ion-implanted into the body of the device. Ordinarily, the technique of ion implanting a device with stable isotopes such as $^{31}$P, $^{185}$Re, $^{89}$Y, or $^{102}$Pd in order to produce $^{32}$P, $^{186}$Re, $^{90}$Y, or $^{103}$Pd, respectively, by subjecting the device to neutron activation cannot be used with activatable substrates, because the neutron bombardment will activate elements, such as chromium, iron, and nickel, in the body to produce long-lived, high-energy gamma ray-emitting isotopes such as $^{51}$Cr and $^{59}$Fe, which are unacceptable in a medical device which is intended to be implanted in a human patient.

The present discovery that, for example, a stent containing about $1.5 \times 10^{16}$ atoms of an isotope with a high neutron activation cross-section such as $^{168}$Yb beneath the surface of the stent can be activated in a nuclear reactor in less than about two hours renders the process feasible even using a stainless steel body. The use of isotopes having extremely large neutron activation cross-sections allows the duration of the activation to be sufficiently short, e.g., less than about two hours, and preferably less than one hour, that iron, chromium, nickel, and other elements in the device body produce negligible contaminating radiation. Similarly, activation of elements such as iron, chromium, and nickel, which may be present in any adhesion coatings, high density coatings, or other layers of the device is minimized during the shortened duration of neutron activation.

The present method of ion-implanting stable (i.e., non-radioactive) high neutron activation cross-section isotopes followed by thermal neutron activation of the stable isotope to generate a radioisotope having desirable therapeutic profiles has several advantages. For example, in a currently preferred embodiment wherein $^{168}$Yb is used, the extremely high thermal neutron activation cross-section of $^{168}$Yb, about 3470 barns, allows a substantial reduction in the time required for neutron activation of the precursor element. Furthermore, this property allows the practical utilization of only about $1.5 \times 10^{16}$ atoms in the near-surface region of the stainless steel body. The nature of ion implantation mass-separates the 0.13% natural abundance of $^{168}$Yb from the remaining isotopes of ytterbium, thereby enriching the activatable isotope. Additionally, the sub-surface implantation is deep enough to provide a sealed source, but not deep enough to allow the device body to absorb the soft x-rays, thereby creating a device which emits a substantial amount of x-rays. Ion implantation of $^{124}$Xe offers similar advantages.

The term "associated with" as used herein to describe the relationship between the body and the radioisotopes or precursors includes relationships such as infusion, coating, mixture, incorporation, interleaving, envelopment, embedding, diffusion, enclosure, adhesion, imprinting, deposition, electroplating, implantation, and melding of one or more elements with one or more other elements, or any other relationship that implies permanence or semi-permanence of that relationship.

The body useful in the medical device of the present invention comprises a structure, device, or article having characteristics, such as stability, resiliency, structure, and shape, suitable for its intended use. The body may comprise a stent, seeds, wire, or other articles suitable for implantation in a patient to deliver a localized dose of radiation. In one embodiment, the body is made from metals and metal alloys, for example, titanium alloy, titanium-vanadium-aluminum alloy, rhodium, vanadium, palladium, rhenium, aluminum, nickel, nitinol (NiTi), stainless steel, and alloys of stainless steel such as type 404. Preferred metal alloys include stainless steel, rhodium, palladium, titanium, Ti-6-4, which is 90% titanium, 6% vanadium, and 4% aluminum, and nitinol, which is 50% nickel and 50% titanium. In another embodiment, the body may comprise one or more materials selected from the group comprising organic polymers and ceramic oxides, such as quartz (silicon dioxide), alumina (aluminum oxide), titania (titanium dioxide), and zirconia (zirconium oxide). A body may further comprise one or more elements, e.g., ytterbium-168, xenon-124, barium-130, phosphorus-31, palladium-102, yttrium-89, rhenium-185, rhenium-187, and tungsten-186, which can be neutron-activated to radioactive isotopes.

Figure 1B:
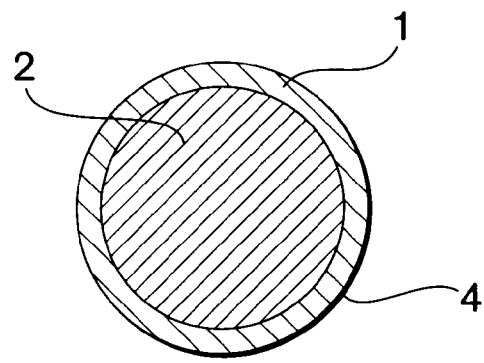
Figure 3:
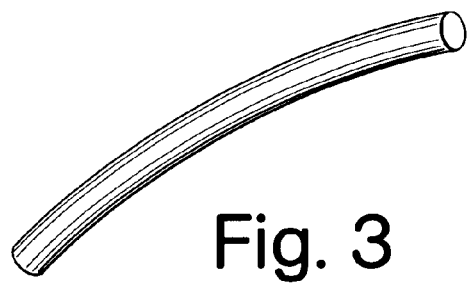
FIG. 3 illustrates a wire, an embodiment of the present invention.

In a currently preferred embodiment, the body comprises a stent, said stent being a medical device that can be placed within the lumen of a tubular structure to provide support during or after anastomosis or catheterization, or to assure patency of an intact but contracted lumen. FIG. 1 shows an example of a stent used in coronary arteries. In this embodiment, the shape of the body may be a tubular mesh shape, a helical coil shape, or any of a variety of other shapes suitable for a stent. In another preferred embodiment, the body comprises a wire, the wire being a medical device that can be inserted into a lumen of a tubular structure to deliver a dose of radiation. FIG. 3 shows an example of such a wire.

The body comprises radioactive isotopes to provide therapeutic or a prophylactic radiation treatment to a subject. For example, a radioactive stent may be implanted in a blood vessel after angioplasty to inhibit restenosis. In one embodiment, the implantable medical device preferably comprises a body that is initially formed from a non-radioactive structural material. One or more stable, non-radioactive precursor isotopes are added into the body or onto the body of the medical device under conditions sufficient to cause the isotope to become associated with the body. The precursor isotopes associated with the body of the medical device are activated by exposing the body to a source of thermal neutrons. In another embodiment, one or more radioactive elements are added to the body or onto the body, thereby eliminating the need for the activation step. In yet another embodiment, coatings that enhance the safety and/or performance of these medical devices may be applied to the devices.

The criteria for selection of a stable precursor element that is to be neutron-activated include: having a half-life between about two and about thirty days, or between about two and about seventy days; having a high neutron activation cross-section; and having the resultant radioisotope primarily emit beta particles or x-rays rather than gamma rays. Beta particles and x-rays provide a short-range dose to tissue, and thus the entire body of the patient does not receive a radiation dose unnecessarily. Radioisotopes that meet these criteria to a greater or lesser extent comprise phosphorous-32, phosphorous-33, sulfur-32, and rhenium-186. Phosphorous-32 has a low neutron activation cross-section, phosphorous-33 is difficult to produce, sulfur-32 has too long a half-life, and rhenium-186 produces 20% of its radiation as gamma rays. Preferred non-radioactive precursor isotopes include ytterbium-168, xenon-124, barium-130, phosphorus-31, palladium- 102, yttrium-89, rhenium- 185, rhenium-187, and tungsten-186, most preferably ytterbium-168 and xenon- 124.

For both $^{168}$Yb and $^{124}$Xe, neutron activation leads to an isotope which is primarily a soft x-ray emitter as a result of electron capture decay. In the case of $^{168}$Yb, the reaction is:

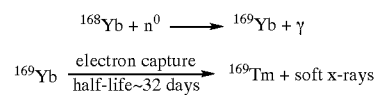

Thus, the stable precursor and the radioactive product are of the same element, i.e., ytterbium.

In the case of neutron activation of $^{124}$Xe, however, the useful radioactive product is a different element, because the process involves a preliminary decay step:

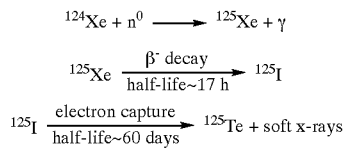

Thus, in the case of $^{124}$Xe, after about 10 half-lives of $^{125}$Xe, i.e., 171 hours or about one week, almost all of the $^{125}$Xe will have decayed to $^{125}$I, which has a half-life of about 60 days and emits essentially pure 31 keV x-rays from electron capture decay without gamma or beta emissions.

The non-radioactive precursor isotope may include some percentage of other isotopes. A non-radioactive precursor isotope may be optionally added to the body of the medical device by either incorporating a small quantity of the isotope into the molten alloy precursor from which the body of the medical device is fabricated, thermally diffusing the isotope into the body of the medical device, ion-implanting with isotope mass separation below the surface of the body of the medical device, or coating the surface of the body of the medical device. Other methods for adding a non-radioactive isotope to the body of the medical device, such as electroplating or sputtering, may also be employed, either alone or in combination.

The quantity of desired non-radioactive isotope to be added to the implantable medical device body varies with the size of the body of the medical device. For example, a typical stent requires about ten to fifty micrograms of rhenium-185 or nearly five milligrams of phosphorous-31, with the difference primarily being related to the activation cross-section and half-life. Adding as much of a desired non-radioactive isotope as possible while avoiding a significant alteration in the desired physical and chemical properties of the medical device body is preferable for minimizing neutron activation time and minimizing the incidental activation of contaminating species in the medical device body. Isotopically enriched additions of non-radioactive precursor isotopes, such as enriched ytterbium, obtained through the use of mass-analyzed ion implantation, may be employed to advantage and are preferred.

When the medical device body is thermal neutron-activated, both the precursor isotope and any activatable impurity isotopes in the body may become radioactive. If the quantity or neutron activation cross-section of a precursor isotope is increased, the required level of the radioactive isotope can be obtained with less neutron activation time. This in turn results in lower radioactivity levels due to impurities in the medical device body. The quantity of non-radioactive precursor isotope is most easily increased by combining several of the methods described for precursor addition. In a preferred embodiment for coatings, another high-density coating material such as rhodium, palladium, or titanium would be sputtered either simultaneously or during a portion of the ion implantation, such that the external surface of the high-density coating would consist solely of a biologically inert element.

Ordinarily, heavy atoms cannot be implanted into steel at doses exceeding $1\times10^{17}/cm^2$ because of the excessive sputtering of material from the surface by the ion beam. At a dose above $1\times10^{17}/cm^2$, the number of heavy atoms incident is equal to the number sputtered away and therefore the heavy atoms cease to accumulate on the body ("Mechanical and Chemical Properties of Tantalum Implanted Steels", Hubler G. K., and Singer I. L., *Materials Science and Engineering*, 60 (1985) 203–210). Ion implantation of $^{124}$Xe, a gas at room temperature, has the additional limitation that the concentration of Xe cannot exceed a certain solubility in the substrate. However, if ion implantation is performed while simultaneously depositing a coating of a second metal or metal alloy (see U.S. Pat. No. 5,383,934, hereby incorporated herein by reference), the sputter loss then consists of atoms from the growing coating rather than those being ion-implanted, yielding improved retention of implanted ytterbium-168 atoms. Using this technique, it is possible to ion implant up to $1\times10^{18}/cm^2$ Yb atoms into a stainless steel stent. In the case of $^{124}$Xe, the simultaneous coating supplies additional material so that the concentration of Xe typically does not exceed 20 atom %. The second metal or metal alloy is preferably chosen from among elements which do not become substantially radioactive when exposed to a source of thermal neutrons. Metals which may be useful in this capacity include, for example, palladium, titanium, and rhodium.

Figure 2:
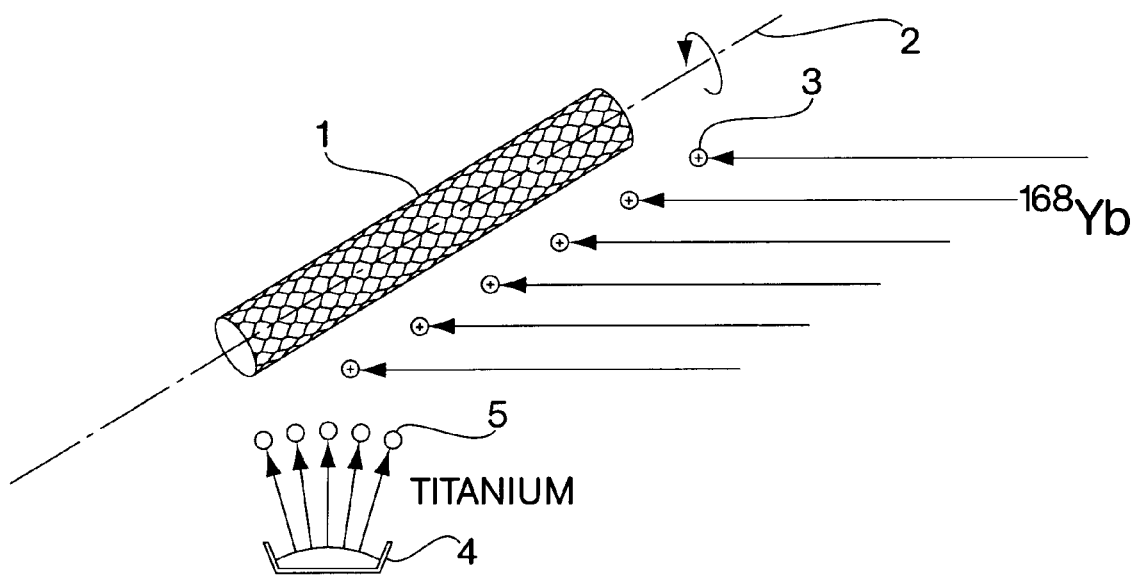
FIG. 2 illustrates a method for ion-implanting $^{168}$Yb into a stent.

An example of the above technique is depicted in FIG. 2. In this exemplary practice, the stent 1 is mounted in a vacuum chamber and rotated about horizontal axis 2 at a speed of approximately 10 rpm. The horizontal $^{168}$Yb ion beam 3 is incident upon the stent with an energy of 90 keV and a current density of approximately 1 $\mu$A/cm$^2$. At this rate, the required dose of $4.3\times10^{16}/cm^2$ can be accumulated in 1.9 hours while depositing a coating approximately 2000 Å thick. Concurrent with the ion bombardment, an evaporation hearth 4 evaporates titanium metal 5 at a rate of 0.3 Å/sec/cm$^2$ for the entire 1.9 hour procedure. The resulting stent will contain approximately $1.5\times10^{16}$ atoms of $^{168}$Yb embedded into its outer surface. Use of this technique for the ion implantation of $^{124}$Xe, wherefor a layer typically between 5 and 20 microns thick is deposited, is similarly advantageous. Procedures achieving an equivalent result will be apparent to those of skill in the art.

The amount of exposure required for neutron activation of the medical device depends on the flux rate of the nuclear reactor used, the thickness and composition of the coating applied to the body, the neutron activation cross-section of the precursor element, and the amount of beta radiation desired. The exposure time could range from a few minutes in a very high flux reactor to several hours in a low flux reactor.

When the radioactive isotopes are produced by neutron activation of the entire medical device in a nuclear reactor, the bulk material of the medical device may also be activated. If the medical device body contains significant quantities of nickel, undesirable long-lived emissions of nickel-63 typically are produced during prolonged periods of activation. This isotope decays solely by beta decay with no gamma radiation. The beta end-point energy is 66.9 keV. Without blocking the nickel-63 beta particles, the particles would continuously bombard the patient for the lifetime of the patient, because the half-life of nickel-63 is 100 years. Reducing the activation time is thus advantageous.

Nickel also is sometimes considered to be a source of undesirable metal ions in the human body. In nitinol, the nickel is stabilized in the form of a compound. In the present invention, it is desirable to provide a coating of a protective, biologically inert material to reduce or eliminate the risk of nickel dissolution into the bloodstream or other bodily fluids.

If the medical device body contains a significant quantity of nickel, a coating of a high-density material may be applied over at least a portion of the body. The coating of high-density material may serve several useful purposes, including containment of undesirable beta particles from long-lived radioactive species, creation of a biologically inert surface, and enhancement of x-ray radiopacity to improve the visibility of the implantable medical device. In a preferred embodiment, a coating of high-density material is used to block the passage of beta particles from nickel-63 into the surrounding tissue by covering essentially all of the exposed surface of the medical device with the high-density material. In one embodiment, the coating of high-density material may be applied prior to neutron activation. In another embodiment, the coating is applied after neutron activation.

If the high-density coating is applied after neutron activation of the medical device body, it may be fabricated in combination or individually of gold, platinum, iridium, or rhenium in addition to those elements that may be used for coating before neutron activation, e.g., rhodium, titanium, vanadium, manganese, copper, and praseodymium. The required properties are high-density, high atomic number, chemical inertness, and adhesion strength. The high-density coating may have a thickness preferably between about 0.01 micrometer and about 30 micrometers, more preferably between 0.01 micrometers and 10 micrometers. If the thickness of the high-density coating is between five micrometers and twenty micrometers, it may also be utilized as a radiopaque material to improve x-ray visibility. In a preferred embodiment, the thickness is greater than the range of 70 keV beta particles, for example about 8.4 micrometers for gold and about 10 micrometers for rhodium. The advantage of applying the high-density coating after neutron activation is the freedom to select the highest density materials. The disadvantage is that personnel must handle a radioactive device during the coating procedure.

An alternate embodiment would involve application of a high-density coating Or to neutron activation of the medical device body. This alternate embodiment requires that the elements in the high-density coating must not activate significantly to any undesired radioisotopes during the required activation period. Minimizing the activation period thus becomes advantageous. If the high-density coating is also to be used for radiopacity, the coating requires sufficient density and thickness to exhibit good x-ray visibility. Examples of such elements, which may be employed in combination or individually, are rhodium, titanium, vanadium, manganese, copper, and praseodymium. Rhodium or an alloy of rhodium-copper are preferred within this group. Rhodium has a density of 12.4, copper has a density of 9.0, and both are mutually miscible in all proportions. The copper is included to increase the ductility and reduce the stiffness of the rhodium. Neutron activation of stable rhodium-103 produces rhodium-104, which has a 4.3 minute half-life. Neutron activation of stable copper-63 produces copper-64, which has a 12.7 hour half-life. Neutron activation of stable copper-65 produces copper-66, which has a 5.1 minute half-life. While rhodium has a lower density than gold or platinum, rhodium is more efficient at attenuating x-rays in the energy range between approximately 30 to 80 keV, which is in the central portion of a 120 keV tungsten bremsstrahlung x-ray spectrum commonly employed for medical imaging. As a consequence, rhodium and gold coatings of equal thickness are typically within five to ten percent of one another in terms of x-ray radiopacity.

In another embodiment, a gold coating is applied to enhance the x-ray image. In a preferred embodiment, a gold coating approximately ten to fifteen micrometers in thickness on the medical device body significantly enhances the x-ray image. Gold is a very soft metal, and a thickness of ten to fifteen microns should not contribute additional structural stiffness to the body of the medical device. If the medical device body is a stent, it should have considerable stiffness in order to hold open the elastic artery. In order to effect good adhesion of the gold coating to the medical device body, it is desirable to first coat the structure with a thin coating of titanium about 3000 Angstroms thick before depositing the thicker gold coating. Titanium has been found to promote adhesion to nitinol stents. Both the adhesion-promoting layer and the gold coating can be deposited using an unbalanced magnetron sputtering process in vacuum.

Optionally, one or more adhesion layers may be disposed on the body to promote adhesion of the non-radioactive precursor isotope, the high-density coating material, and/or the radioactive isotope. The adhesion layer may be formed a material that includes silicon, aluminum, titanium, vanadium, nickel, praseodymium, or rhodium when used between the body and the non-radioactive precursor isotope or the radioactive isotope. The adhesion layer preferably comprises silicon, titanium, vanadium, chromium, iron, cobalt, or nickel when used between the body of the medical device and the high-density coating material.

The selection of high-density coating materials and adhesion layer materials is dependent on whether these materials will be subjected to neutron activation and the duration of said neutron activation period. Preferably, the therapeutic isotopes will have half-lives between one day and forty days. If materials in either the high-density coating or the adhesion layer are susceptible to being neutron-activated to radioactive isotopes, it is preferable that the half-lives of any such radioactive isotopes be shorter than about one day, so that these isotopes can be expected to decay to insignificant activity levels before the device is implanted. The elements aluminum, silicon, titanium, vanadium, manganese, copper, praseodymium, and rhodium meet the criterion of short half-life.

The following example further illustrates the invention, and is not intended to be limiting in any way.

EXAMPLE 1

A conventional stainless steel stent (available from Guidant Corp. Multilink, or Cordis) can be processed according to the following example:

stent mass: 0.01 5 gram material: 316L stainless steel surface area: 0.35 $cm^2$ $^{168}$Yb ion implant dose: $4.3 \times 10^{16}/cm^2$ ion implantation energy: 90 keV simultaneous coating of Ti: 2000 Å

$^{168}$Yb atoms in surface: $1.5 \times 10^{16}$ atoms thermal neutron dose rate: $8 \times 10^{13}$ neutrons/$cm^2$/sec thermal neutron dose duration: 1 hour post-activation decay time: 7 days $^{169}$Yb initial activity: 84 $\mu$Ci The resulting stent produces a total dose to the adjacent tissue of approximately 25 Grays 2 mm from the outer surface of the stent, which is within the accepted therapeutic range.

Exposure to neutron activation preferably does not activate the stainless steel stent body significantly. Indeed, when the stent is activated for one hour at a neutron dose rate of $8 \times 10^{13}$ neutrons/$cm^2$/sec, the total gamma ray activity from the alloy constituents is:

From 74% iron in stainless steel: 0.5 µCi of $^{59}$Fe

From 18% chromium in stainless steel: 3.5 µCi of $^{51}$Cr

From 8% nickel in stainless steel: 0.009 µCi of $^{63}$Ni

Other trace contaminants such as Mn and Si produce even less radioactivity.

EXAMPLE 2

For temporary intra-vascular brachytherapy, a 2.5 cm-long wire can be prepared which emits only soft x-rays (32 keV) from $^{125}$I using the following parameters:

wire diameter: 0.010 inch material: rhodium $^{124}$Xe atoms in surface: 1×10$^{18}$ atoms ion implantation energy: 90 keV simultaneous coating of Ti: 15 microns thermal neutron dose rate: 2×10$^{15}$ neutrons/cm$^2$/sec thermal neutron dose duration: 30 days post-activation decay time: 7 days $^{125}$I initial activity: 7 Ci Activity per unit length: 2.8 Ci/cm The resulting wire source, when placed into an angioplasty site using an appropriate catheter, can provide a dose of 25 Grays 2 mm from the wire in less than 30 minutes, which is within the accepted therapeutic range.

Equivalents

While the invention has been disclosed in connection with the preferred embodiments shown and described in detail, various equivalents, modifications, and improvements will be apparent to one of ordinary skill in the art from the above description. Such equivalents, modifications, and improvements are intended to be encompassed by the following claims.

What is claimed is:

1. A medical device comprising a body and at least one isotope associated with the body, wherein the isotope has a neutron activation cross-section of at least about 3000 barns, whereby thermal neutron activation of the isotope generates a therapeutically effective amount of a radioactive isotope.

2. The device of claim 1, wherein said body comprises a material selected from the group consisting of organic polymers, ceramic oxides, metals, and metal alloys.

3. The device of claim 1, further comprising a high-density coating applied to at least a portion of the body.

4. The device of claim 3, further comprising an adhesion coating disposed between said body and said high density coating.

5. A medical device comprising a body and $^{168}$Yb associated with said body, whereby thermal neutron activation of the $^{168}$Yb generates a therapeutically effective amount of $^{169}$Yb.

6. The device of claim 5, wherein the $^{168}$Yb is ion-implanted.

7. The device of claim 5, wherein the amount of ytterbium associated with the body is between about 1×10$^{15}$ and about 5×10$^{17}$ atoms.

8. The device of claim 5, wherein the concentration of ytterbium associated with the body is at least about 1×10$^{16}$ atoms/cm$^2$.

9. A medical device comprising a body and $^{124}$Xe associated with said body.

10. The device of claim 9, wherein the $^{124}$Xe is ion-implanted.

11. The device of claim 9, wherein said body comprises stainless steel, titanium, or nitinol.

12. The device of claim 9, wherein said body comprises rhodium, palladium, or a palladium alloy.

13. The device of claim 9, wherein the amount of $^{124}$Xe associated with the body is between about 1×10$^{17}$ and about 5×10$^{18}$ atoms per centimeter of length.

* * * * *